United States Patent [19]

Bergström et al.

[11] Patent Number: 5,242,828
[45] Date of Patent: Sep. 7, 1993

[54] SENSING SURFACES CAPABLE OF SELECTIVE BIOMOLECULAR INTERACTIONS, TO BE USED IN BIOSENSOR SYSTEMS

[75] Inventors: Jan Bergström, Bälinge; Stefan Löfas, Uppsala; Bo Johnsson, Storvreta, all of Sweden

[73] Assignee: Pharmacia Biosensor AB, Uppsala, Sweden

[21] Appl. No.: 681,531

[22] PCT Filed: Nov. 9, 1989

[86] PCT No.: PCT/SE89/00642

§ 371 Date: May 10, 1991

§ 102(e) Date: May 10, 1991

[87] PCT Pub. No.: WO90/05303

PCT Pub. Date: May 17, 1990

[30] Foreign Application Priority Data

Nov. 10, 1988 [SE] Sweden ............................... 8804073

[51] Int. Cl.$^5$ ..................... G01N 21/00; C12M 1/34
[52] U.S. Cl. ..................... 435/291; 435/808; 422/57; 422/58; 422/82.05; 422/82.11
[58] Field of Search ............. 422/57, 58, 69, 82.11, 422/82.05; 435/808, 291; 356/318, 445; 385/12

[56] References Cited

U.S. PATENT DOCUMENTS

| | | | |
|---|---|---|---|
| 3,912,614 | 10/1975 | Spracklen et al. | 204/195 B |
| 4,842,783 | 6/1989 | Blaylock | 264/1.4 |
| 4,857,273 | 8/1989 | Stewart | 422/68 |
| 4,877,747 | 10/1989 | Stewart | 436/525 |
| 4,931,384 | 6/1990 | Layton et al. | 435/7 |
| 4,992,385 | 2/1991 | Godfrey | 436/525 |
| 4,997,278 | 3/1991 | Finlan et al. | 356/128 |

FOREIGN PATENT DOCUMENTS

| | | |
|---|---|---|
| 0226470 | 6/1987 | European Pat. Off. |
| 0254430 | 1/1988 | European Pat. Off. |
| 0254575 | 1/1988 | European Pat. Off. |
| 0276142 | 7/1988 | European Pat. Off. |
| 0339821 | 11/1989 | European Pat. Off. |

OTHER PUBLICATIONS

Bain et al. (1988) J. Am Chem. Soc., 110:5897–5898.
Bain et al. (1988) Science, 240:62–63.
Troughton, et al. (1988) Langmuir, vol. 4, No. 2, pp. 365 and 377.
Porter et al. (1987) J. Am Chem Soc. 109.3559, 3568.
Troughton et al, Langmuir, vol. 4, pp. 365–385 (1988).
Cullen et al, Biosensors, vol. 3, pp. 211–225 (1987/1988).
Strong et al, Langmuir, vol. 4, pp. 546–558 (1988).

*Primary Examiner*—Robert J. Warden
*Assistant Examiner*—T. A. Trembley
*Attorney, Agent, or Firm*—Birch, Stewart, Kolasch & Birch

[57] ABSTRACT

A sensing surface suitable for use in a biosensor, comprising:
  a film of a free electron metal selected from the group consisting of copper, silver, aluminum and gold; and
  a densely packed monolayer of an organic molecule X-R-Y coated on one of the faces of said film where X is a group selected from the group consisting of
  asymmetrical or symmetrical disulfide (—SSR'Y', -SSRY, sulfide (-SR'Y', -SRY), diselenide (-SeSeR'Y', -SeSeRY), selenide (SeR'Y', -SeRY),
  thiol (-SH), isonitrile, nitro (-NO$_2$), selenol (-SeH), trivalent phosphorus compounds, isothiocyanate, xanthate, thiocarbamate, phosphine,
  thio acid and dithio acid (-COSH, -CSSH)
  where R and R' are hydrocarbon chains optionally interrupted by hetero atoms, of a length exceeding 10 atoms, wherein in the case of an asymmetrical molecule, R' or R may be H, and Y and Y' are active groups for covalently binding ligands or a biocompatible porous matrix.

27 Claims, 4 Drawing Sheets

SENSING SURFACES CAPABLE OF SELECTIVE BIOMOLECULAR INTERACTIONS, TO BE USED IN BIOSENSOR SYSTEMS

BACKGROUND OF THE INVENTION

1. Field of the Invention

The present invention relates to the field of biosensors and is more specifically concerned with methods for providing metal surfaces with surface layers capable of selective biomolecular interactions. The invention also comprises activated surfaces for coupling a desired ligand; surfaces containing bound ligand; and the use of such surfaces in biosensors.

2. Description of Related Art

According to Aizawa (1983) a biosensor is defined as being a unique combination of a receptor for molecular recognition, for example a selective layer with immobilized antibodies, and a transducer for transmitting the interaction information to processable signals. One group of such biosensors will detect the change which is caused in the optical properties of a surface layer due to the interaction of the receptor with the surrounding medium. Among such techniques may be mentioned especially ellipsometry and surface plasmon resonance. In order for these types of techniques to work satisfactorily in actual practice certain requirements have to be fulfilled—i.e., the requirement that the sensing surface (or measuring surface) employed can easily be derivatized so that it will then contain the desired receptor, and moreover that it will not produce any (or only negligible) non-specific binding, i.e., binding of components other than those that are intended. In somewhat simplified terms the technique of surface plasmon resonance—by abbreviation SPR, as derived from the initials surface plasmon resonance may—may be said to be a technique in which changes in the refractive index in a layer close to a thin metal film are detected by consequential changes in the intensity of a reflected light beam (see for example Raether, H (1977).

Thus in this case, the sensing surface is a metal like film with receptors or "ligands" as they will be called henceforth, these being generally molecules or molecular structures which interact selectively with one or more biomolecules.

The metal film is applied on a substrate of a type that is suitable for the measuring method employed In the case of SPR, this means that a dielectric material, e.g., in the form of a glass plate, is used for directing a light beam to the metal surface.

According to most of the publications that have come forth up to now, SPR procedures when applied to detecting biomolecules have been carried out simply by adsorbing the biomolecule in question directly to the metal surface and then studying the consequential effect on the measuring signal. In a next step, this surface could optionally be used for binding a new layer of molecules (ligands) having an affinity for the first-bound layer of molecules. Thus for instance Liedberg, B. et al. (1983), in a first work indicating the potential of SPR technology for biochemical analyses, adsorbed at first a monolayer of IgG to a silver surface and then adsorbed an anti-IgG layer to said monolayer, in order to then study the effect with respect to the resultant change in the resonance angle.

Others too, e.g., Cullen DC et al. (1987/88), have utilized adsorption of biomolecules directly to a metal surface when studying immune complex formation in the IgG/anti-IgG system using the SPR technique with a gold-coated diffraction grating.

EP 257g55 describes a method according to which the metal film is coated with silica and optionally treated with a silanizing reagent; and in EP 202021 the metal film has been coated with an organic layer that may contain for example an antibody to a specific antigen Although the possibility of the antibody being bound covalently is indeed mentioned in that specification the actual nature of the organic layer is not disclosed or indicated at all, and the same applies to the manner in which the organic layer is produced.

According to EP 254575 an optical structure of the type such as is suitable for e.g. SPR applications may be produced by coating the metal film with a layer of an organic polymer, by means of the so-called "solvent casting technique" In a preferred embodiment cellulose nitrate is employed, and a number of well-known methods are mentioned for binding biospecific ligands to the layer.

Publications of this kind, while giving indications of the potential of the method, also demonstrate some of the limitations inherent in the technical solutions proposed.

As pointed out in for instance EP 254575, one of the problems is that biomolecules may be subject to an at least partial inactivation due to direct contact with metallic and certain inorganic surfaces. Another complication is that some ligands which may be desirable for some special applications cannot be adsorbed in a stable manner to a metal surface and thus cannot be expected to give reproducible results. Still another problem is that many of the media occurring in biochemical systems have a corrosive effect on the metal surface.

Although problems of these kinds may be solved at least in part by way of a process according to EP 254575, a construction of this type has a number of obvious drawbacks. A polymeric coating in the form of cellulose nitrate—as according to a preferred embodiment—will put a limit on the number of possible applications inasmuch as it is a well-known fact that biomolecules can be adsorbed irreversibly to cellulose nitrate films. In biosensor systems based on optical surface detection technology such a phenomenon may give rise to ambiguous and non-reproducible signals due to non-specific interaction between the sensing surface and components present in, for instance, human serum samples. Such side effects have been compensated for in EP 254575 by using a combination of a measuring and a reference surface. A requirement for the working of this method is that the nonspecific contribution is equally great on both surfaces; but this condition is not always fulfilled in actual practice.

Another problem is pointed out in EP 226470 regarding the production of constructs similar to the one mentioned above (see also U.S. Pat. No. 4415666). From the specification it can be seen how difficult it is to obtain acceptable stability, uniformity and reproducibility of the polymeric coating; and the consequential negative effects in cases where biosensor systems are employed will be readily appreciated.

Although for many practical uses a polymeric coating of the cellulose nitrate type having a thickness of 15-20 nm may indeed provide sufficient protection from corrosion, there is nevertheless an obvious risk that smaller molecules may penetrate through such a layer and cause an irreversible change in the metal surface. As shown below, sulfur compounds such as will be encountered in some situations associated with the present type of measurements—e.g., in cases where organic thiol compounds are used for reducing disulfide bonds in proteins—have a high affinity for noble metals, and upon being adsorbed will produce an uncontrolled alteration of the optical properties of the metals. It has also been shown that a polymeric coating of the cellulose nitrate type may be damaged by, e.g., detergent treatment with 2% SDS (see EP 254575).

SUMMARY OF THE INVENTION

A generally useful sensing surface for biosensor systems, especially SPR, should fulfill the following desiderata:

It should be chemically resistant to the media employed.

It should be compatible with proteins and other biomolecules and should not interact with any molecules other than those desired.

It should be capable of providing for covalent binding of such a large number of ligands as is required for a general applicability of this technique to a variety of analytical problems.

For the sake of obtaining a high degree of sensitivity and dynamics, the surface should provide a tridimensional matrix for the sample solution for binding the target molecules therein. In this manner a greater part of the volume influencing the resonance effect, by way of its refractive index, will be utilized as compared to cases where a two-dimensional surface would be used.

We have now constructed a surface which in its preferred embodiment will fulfill all of these desiderata quite well.

Further scope of the applicability of the present invention will become apparent from the detailed description and drawings provided below. However, it should be understood that the detailed description and specific examples, while indicating preferred embodiments of the invention, are given by way of illustration only since various changes and modifications within the spirit and scope of the invention will become apparent to those skilled in the art from this detailed description.

BRIEF DESCRIPTION OF THE DRAWINGS

The above and other objects, features, and advantages of the present invention will be better understood from the following detailed descriptions taken in conjunction with the accompanying drawings, all of which are given by way of illustration only, and are not limitative of the present invention, in which.

DETAILED DESCRIPTION OF THE INVENTION

The followed detailed description of the invention is provided to aid those skilled in the art in practicing the present invention. Even so, the following detailed description should not be construed to unduly limit the present invention, as modifications and variations in the embodiments herein discussed may be made by those of ordinary skill in the art without departing from the spirit or scope of the present inventive discovery.

The metal surface is constituted by a film of a free electron metal such as e.g. copper, silver, aluminum or gold. These metals give different resonance effects, and although silver is very good in this respect we have nevertheless decided —in view of corrosion stability considerations—that gold should be the preferred metal. For binding the desired biospecific ligand we have applied a monolayer of an organic molecule X-R-Y to the metal surface. This monolayer is densely packed on the surface, and in addition to being used for binding the ligand it forms an efficient barrier layer which is very stable upon storage and protects the metal surface from chemical corrosion.

Generally, modification of gold surfaces with certain types of sulfur compounds has been described by, for example, Nuzzo RG et al. (1983), Porter MD et al. (1987), and Troughton EB et al. (1988).

X-R-Y in the form of a densely packed monolayer becomes attached to the metal in conformity with the principles described in the above-cited publications, the bonds being partially covalent in character; X binds to the metal and Y serves for coupling with functional ligands. This may be effected either in that the ligand is coupled directly to Y, optionally after activation of Y, or in that a biocompatible porous matrix like for instance, a hydrogel, is bound to the barrier layer via Y whereupon this matrix is utilized for binding the ligand.

X belongs to one of the following groups:

asymmetrical or symmetrical disulfide (-SSR'Y', -SSRY), sulfide (-SR'Y', -SRY), diselenide (-SeSeR'Y', -SeSeRY), selenide (-SeR'Y', -SeRY), thiol (-SH), nitrile (-CN), isonitrile, nitro (-NO$_2$), selenol (-SeH), trivalent phosphorous compounds, isothiocyanate, xanthate, thiocarbamate, phosphine, thioacid or dithioacid (-COSH, -CSSH).

R (and R') is (are) a hydrocarbon chain which may optionally be interrupted by hetero atoms and which is preferably straight (=non-branched) for the sake of optimum dense packing, and contains optionally double and/or triple bonds. The length of the chain exceeds 10 atoms. Shorter chains will yield layers of poorer stability. Chain lengths of 12–30 atoms are currently preferred. The carbon chain may optionally be perfluorinated.

Y and Y', which are preferably the same have properties such that they can bind the target substance directly or after activation. Y (and Y') may thus be any among the great number of groups which are used for immobilization in liquid chromatography techniques, for instance a hydroxyl, carboxyl, amino, aldehyde, hydrazide, carbonyl, epoxy or vinyl group. There are many articles to be found in the literature dealing with coupling of various ligands such as, e.g., biomolecules, with the aid of these or other groups; available alternatives of choice will therefore be readily obvious to persons skilled in the art.

An obvious variant of this concept involves adsorbing a mixture of different organic molecules X-R-Y. This may be done for the purpose of obtaining an increased capacity for further derivatization or for the purpose of obtaining multifunctional surfaces. Furthermore, the barrier layer may be formed by means of various types of more complex molecules such as, for instance, molecules containing two or more carbon chains linked to each other in a manner as described by Regen SL et al. (1986).

By crosslinking the molecules in the barrier layer, its stability could be further increased, if necessary. This could be achieved via functional groups in R or Y, for instance by photoinitiated polymerization of double or triple bonds in R; see for instance Ringsdorf H et al (1988).

If the desired ligand or biomolecule is bound directly via Y to the barrier layer several among the above-mentioned desiderata have been fulfilled, and acceptable results are obtainable in at least some practical application instances. According to a preferred embodiment, however, a biocompatible porous matrix like, for instance, a hydrogel, is coupled to the barrier layer, and this matrix, which has a thickness of from a few angstroms to several thousand angstroms, is employed for immobilizing a ligand that is suitable for the target biomolecule. In actual practice the thickness of the matrix layer is chosen so as to suit the dimension of the measuring signal in the measuring space of the measuring system employed, to thus create an optimum set of detection conditions. In SPR applications, the thickness of the matrix layer is preferably 5 to 10,000 angstroms, especially 5 to 1,000 angstroms. A considerably higher ligand density per area unit is obtained in a matrix as described here compared to the prior art technique, in which binding of molecules occurs mainly in monolayers, thus giving a considerably enhanced measuring signal, making the system useful in a larger dynamic range.

The hydrogel in the form as contemplated here and which at present is the preferred embodiment of the matrix, may be defined as according to Merrill et al. (1986). Hydrogel coupling is essential for obtaining a sensing surface fulfilling above all the aforesaid desiderata with respect to protein compatibility and minimized nonspecific interaction. Merrill et al. have described a large number of examples showing such properties in the hydrogel surfaces. Depending on the actual practical application contemplated, any particular hydrogel may be chosen from among several available alternatives of choice.

The hydrogel may be for example a polysaccharide such as agarose, dextran, carrageenan, alginic acid, starch, cellulose, or derivatives of these such as, e.g., carboxymethyl derivatives, or a water-swellable organic polymer such as, e.g., polyvinyl alcohol, polyacrylic acid, polyacrylamide, polyethylene glycol.

In particular, polysaccharides of the dextran type which are non-crystalline in character, in contrast to e.g., cellulose, are very suitable in these contexts. Dextran has been used to a very great extent in chromotographic procedures as a matrix for the binding of biomolecules; one of the advantages inherent in the present concept is actually that this entire technology is now available also for biosensor applications, viz., for the final step of the biosensor technique in which a suitable ligand is being immobilized. The hydrogel may either be bound to the barrier layer "metal-X-R-Y" or may be generated in situ from a suitable solution of monomeric material. Further alternative treating steps such as, for example, subsequent crosslinking of the hydrogel, will naturally be readily obvious to persons skilled in the art.

This type of surface modification can be utilized also in other fields of technology where a specific, or alternatively, a low non-specific, interaction is required between a surface on one hand and proteins or other biomolecules on the other hand. Examples that may be mentioned are parts of chromatographic systems for biomolecule separations where, e.g., metal filters may have their surface modified in a manner as indicated above. It would also be possible to construct capillary-type chromatographic columns in conformity with these principles. Furthermore, it is evident that a surface structure may be modified so as to acquire biocompatibility, for use in environments of the "in vivo" type. Depending on the particular field of use contemplated, the actual choice of, for example, the hydrogel, can be made such that undesired interactions are minimized. To those skilled in the art, a number of additional fields of use will be readily obvious, along the lines of the aforesaid examples.

According to an embodiment further illustrating the invention, a layer of 16-mercaptohexadecanol is bound to the gold film whereupon the hydroxyl groups on the barrier layer are epoxy-activated by means of being treated with epichlorohydrin. In a subsequent step, dextran is attached to the barrier layer via ether linkages. The dextran matrix is next activated for binding ligands according to known techniques, for example in accordance with one of the following principles.

In one embodiment, a hydrazide function is created in the dextran matrix for binding ligands containing aldehyde groups, for example antibodies in which the carbohydrate chain has been oxidized so that it then contains an aldehyde function. In this instance, the dextran matrix is initially modified with carboxymethyl groups which are partly reacted to form hydrazide groups. With this activated matrix at least two important advantages are obtained 1) This matrix contains unreacted carboxyl groups which in low ionic strength conditions will act as ion exchangers, and by electrostatic interaction the ligand which is to be immobilized is concentrated to the dextran matrix. 2) This matrix will very efficiently bind the ligand thus concentrated at the surface, viz. by condensation of ligand aldehyde groups with the hydrazide function of the matrix.

According to another embodiment, a part of the carboxyl groups in carboxymethyl-modified dextran are modified so as to give reactive ester functions, e.g., by treatment with an aqueous solution of N-hydroxysuccinimide and N-(3-dimethylaminopropyl)-N'-ethylcarbodiimide hydrochloride. In the same way as in the case described above, the residual charges id est unreacted carboxyl groups will contribute to effecting a concentration of ligands on the surface. Ligands containing amine groups such as, for example, proteins and peptides may then be coupled to the dextran matrix by covalent bonds.

According to an alternative procedure, the aforesaid reactive ester is utilized for reaction with a disulfide-containing compound such as for instance 2-(2-pyridinyldithio) ethanamine; in this manner a matrix is obtained which contains disulfide groups, and these can be employed for coupling thiol-containing ligands such as for example reduced F(ab) fragments of immunoglobulins (see Brocklehurst K et al (1973)). After cleavage of the disulfide bonds, for instance by reduction or thioldisulfide exchange, the thiol modified surface formed can be used for coupling of a disulfide-containing ligand such as, for instance, N-succinimidyl 3-(2-pyridinyldithio) propionate (SPDP) modified proteins.

The advantage of this procedure is that the ligands via, for example, a reduction step can be cleaved off to give a sensing surface with reactive thiols. This thiol-modified surface can in an analogous procedure be used for renewed covalent coupling of thiol- or disulfide-containing ligands. In this way the capability of chemical regeneration of the sensing surface can be obtained, which can be used for general utilization of the same surface for couplings of several different ligands. The procedure can also be used when, for example a biological interaction is studied, and this interaction cannot be broken while retaining biological activity of the immobilized ligand.

One important aspect of the present invention is that one or more of the layers forming the sensing surface to be used in a given analysis can be synthesized and/or functionalized in situ by adding the appropriate reagents to the surface in a flowthrough cell in a biosensor system.

To sum up, there are a multitude of ligands that can be employed for the detection of biomolecules by means of interacting therewith. It will be readily evident that ion exchanging groups, metal chelating groups and various types of receptors for biological molecules—such as are known from conventional liquid chromatographic procedures—may be employed for the construction of systems which are suitable for selection purposes even in complex measuring systems.

This novel type of sensing surfaces permits measurements to be carried out in systems comprising multiple sensing surfaces for analysing a plurality of sample components; in such a system a very high degree of versatility is obtained if each particular sensing surface is functionalized in situ so as to acquire its desired specificity. In this case, such a sensing surface initially contains an activated dextran layer; functionalization is effected by means of passing the appropriate ligand solutions over each respective one of the sensing surfaces Thereafter the sample solutions are passed over the multiple sensing surfaces, and bound components are detected.

A sensor unit having at least two sensing surfaces, as well as a method for its functionalization, is the object of copending PCT application entitled "Sensor unit and its use in biosensor systems" (based upon Swedish patent application No. 8804074-6), the disclosure of which is incorporated by reference herein.

In one embodiment, so-called chimaeric molecules (bi- or polyfunctional molecules) are used for functionalizing the sensing surfaces. The chimaeric molecules comprise one part that will bind to the basal surface, for example to the aforesaid dextran-coated sensing surface, and one part having an affinity for the biomolecule to be detected. In the case of dextran, the chimaeric molecule may consist of an antibody to dextran which is conjugated to a biospecific ligand, e.g., an immunoglobulin. With a series of such chimaeric molecules, which thus contain a dextran antibody and a group of a different specificity, a so-called measuring cassette containing several sensing surfaces of the same type in one instrument may be activated in a simple manner for parallel detection of a plurality of biomolecules. According to an alternative process, a sensing surface is modified with a so-called hapten for binding chimaeric molecules to the surface. For example, a reactive ester surface as described above may be derivatized with a theophylline analogue which is then employed for binding chimaeric molecules. In this case the chimaeric molecule consists of an antibody directed against theophylline and conjugated with a biospecific ligand. In light of these embodiments, it will be eminently clear that a high degree of versatility is attainable when surfaces according to the present invention are used, inasmuch as the users can to employ identical basal surfaces for attaching thereto any of their desired ligands (TM the desired receptor) by way of a simple procedure.

The invention relating to (i) the aforesaid methods for providing metal surfaces with surface layers capable of selective biomolecular interactions, to be used in biosensor systems, (ii) the above-described surfaces, and (iii) their use in biosensors will now be illustrated by means of the following examples, which are non-limitative. The metal, of course, is applied to a substrate that is suitable for the particular measuring method contemplated in each instance; e.g., a glass plate in the case of SPR. In view of the fact that the selection of the substrates does not form part of this invention, the following exemplification as well as the present specification as a whole deals only with the sensing surface as such, id est the free metal surface with the attached layers thereon.

The sensing surfaces of the invention can be used in various biosensor systems and especially in SPR, e.g., of the type described in copending PCT application entitled "Optical Biosensor System" (based upon Swedish patent application No. 8804075-3), the disclosure of which is incorporated by reference herein.

I. Examples of Producing the Sensing Surface

I.1 Synthesis of 16-mercaptohexadecanol 16-mercaptohexadecanol was synthesized in accordance with the following reaction scheme:

The 16-mercaptohexadecanoic acid methyl ester (IV) was prepared according to well-known methods (Crossland RK et al. (1970), Ghosh SS et al. (1987) and Volante Rp (1981), plus references cited in these publications).

Reduction of (IV) to 16-mercaptohexadecanol was carried out as follows:

16-mercaptohexadecanoic acid methyl ester, 12.0 g (41.7 mmol) dissolved in 70 ml of toluene was added cautiously, dropwise and with vigorous stirring, to 70 ml (70 mmol) of lithium aluminum hydride -bis-tetrahydrofuran (1M) in toluene. During this addition the temperature was maintained below 25° C. The reaction was allowed to proceed at room temperature for 20 minutes. Excess hydride was decomposed by means of ethyl acetate followed by 100 ml of 2M hydrochloric acid. The layers were separated. The aqueous layer was extracted with 100 ml of toluene. The combined organic layers were washed with 100 ml of 2M sodium hydrogen carbonate, dried with magnesium sulfate and evaporated.

Yield: 10.0 g (87.2%); purity 96% according to GLC.

The product was purified by repeated recrystallization from methanol. A purity of >99 % has been considered acceptable. Melting pt 55.0–56.0° C.

I.2 Basic coupling of Au-coated glass surfaces

I.2.1 Chemisorption of 16-mercaptohexadecanol

A 5" gold-coated glass wafer was placed into a petri dish (i.d. 16 cm) provided with a cover. 40 ml of a 5.0 mM solution of 16-mercaptohexadecanol in ethanol/water 80/20 were poured over the surface. The petri dish was incubated on a shaker incubator at 40° C. for 20 minutes. The surface was washed with 5×50 ml ethanol, 50 ml ethanol/water 80/20, and 5×50 ml water. Cyclic voltametric analysis of the surface showed the film to effectively prevent oxidation of the gold.

I.2.2 Treatment with epichlorohydrin

The surface coated with 16-mercaptohexadecanol was contacted with a solution of 2.0 ml of epichlorohydrin in 20 ml of 0.4M sodium hydroxide and 20 ml of diethylene glycol dimethyl ether. Reaction was allowed to proceed in a shaker incubator at 25° C. for 4 hours. The surface was washed with 3×50 ml water, 2×50 ml ethanol, and 5×50 ml water.

I.2.3 Treatment with dextran 13.5 g of dextran (T500, Pharmacia) were dissolved in 40.5 ml of water. 4.5 ml of 1M sodium hydroxide were added and the solution was poured over an epichlorohydrin-treated surface. This was followed by 20 hours of incubation in a shaker incubator at 25° C. The surface was washed with 15×50 ml of 50° C. water.

I.3 Derivatization of basal surfaces

I.3.1 Synthesis of a hydrazide surface

Bromoacetic acid, 3.5 g, was dissolved in 27 g of 2M sodium hydroxide solution The mixture was poured over a dextran-treated surface according to I.2.3 and incubated in a shaker incubator at 25° C. for 16 hours. The surface was washed with water, whereupon the aforesaid procedure was repeated once.

After having been washed, the surface was given a 5 min. treatment with 0.8 g of N-(3-dimethylaminopropyl)-N'-ethylcarbodiimide hydrochloride (EDC) in 20 ml of water, followed by an addition of 4.0 ml of hydrazine hydroxide in 20 ml of water. The surface was incubated in a shaker incubator at 25° C. for 16 hours and then washed with water.

I.3.2 Synthesis of a surface having a reactive ester function 0.69 g of N-hydroxysuccinimide and 1.15 g of EDC were dissolved in 30 ml of water. The mixture was poured over a carboxymethyl-modified dextran surface according to I.3.1 and incubated in a shaker incubator at 25° C. for 60 minutes. The surface was washed with water.

I.3.3 Synthesis of theophylline surface

A solution of 5 mM 8-(3-aminopropyl)-theophylline (R.C. Boguslaski et al., 1980) in 0.1 M carbonate buffer, pH 8.0, was incubated with an N-hydroxysuccinimide ester activated dextran surface (according to Example I.3.2) overnight at 25° C., whereupon the surface was washed with water.

II Coupling of ligands to derivatized basal surfaces

II.1 Anti-IgE antibody

Anti-IgE antibody (Pharmacia Diagnostics AB) in 10 mM acetate buffer, pH 5.5, was oxidized with 10 mM sodium periodate for 20 minutes on an ice bath as according to the method described by O'Shannessy (1985). After replacement of the buffer, the antibody was coupled to the hydrazide-modified dextran surface (Example I.3) in 10 mM acetate buffer, pH 4.0. Antibody that had not been bound was eluted with 0.1 M glycine, pH 2.5.

II.2 Antibeta-2-microglobulin antibody

Antibeta-2-microglobulin antibody (Pharmacia Diagnostics AB) was oxidized and coupled as in Example II.1 to the hydrazide-modified dextran surface.

II.3 Rabbit anti-mouse light chain antibody (RAMLC

RAMLC antibody in 10 mM acetate buffer, pH 5.5 (Pharmacia Diagnostics AB) was coupled for 20 minutes to an N-hydroxysuccinimide ester derivatized dextran surface (according to Example I.3.2), whereupon unbound antibody was washed off by rinsing of the surface in PBS buffer, pH 7.4, and in 0.1 M glycine, pH 2.5.

III Biomolecule assays using the SPR technique

The sensing surface was introduced into an SPR measuring device with a flow cell. After adjustment of the optical instrumentation, the measurement signal was studied as a function of time under constant flow conditions.

Figure 1:
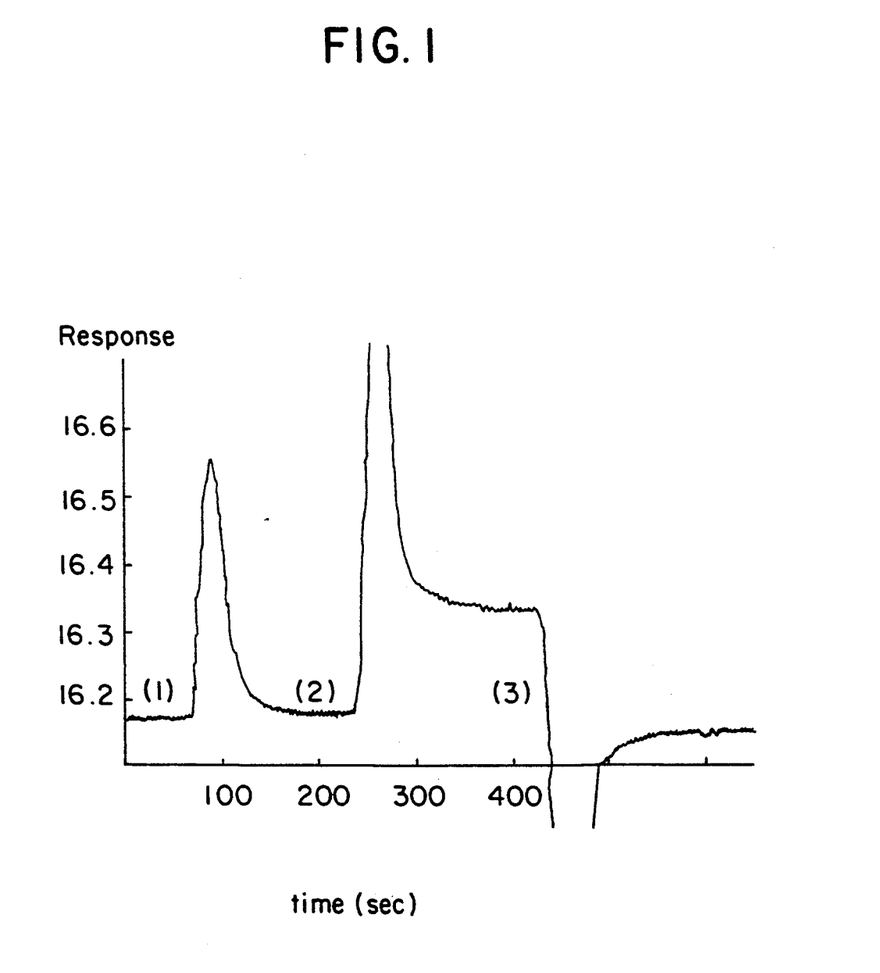
FIG. 1 shows the response curve obtained with (1) injection of culture medium, (2) injection of culture medium containing monoclonal antibody, and (3) regeneration with 0.1 M glycine, pH 2.5, upon injection after covalent immobilization of rabbit anti-mouse light chain (RAMLC) antibodies onto the sensing surface described in Example II.3.
Figure 2:
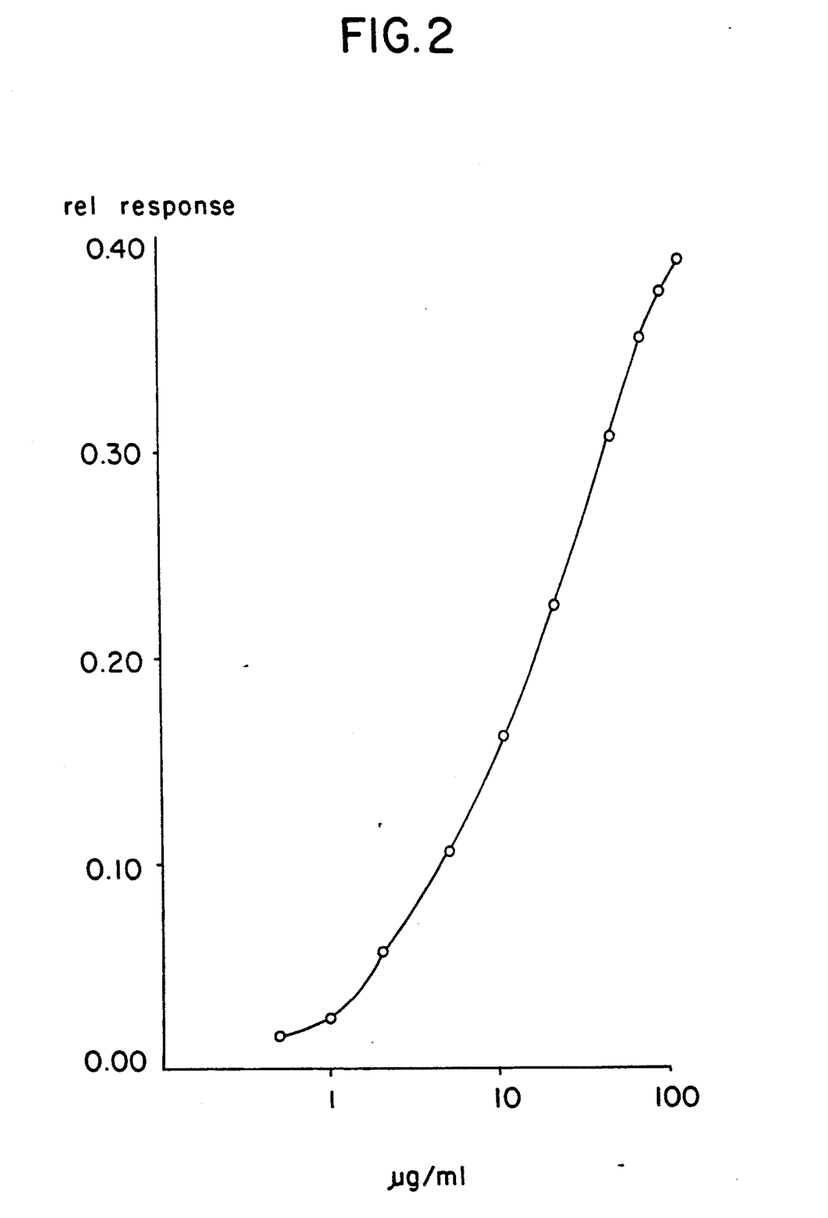
FIG. 2 shows the standard curve for various concentrations of a monoclonal IgG1 antibody. Within the range of 5–100 $\mu$g antibody per ml, the accuracy of the dose-response curve is better than $\pm 10\%$.
Figure 3:
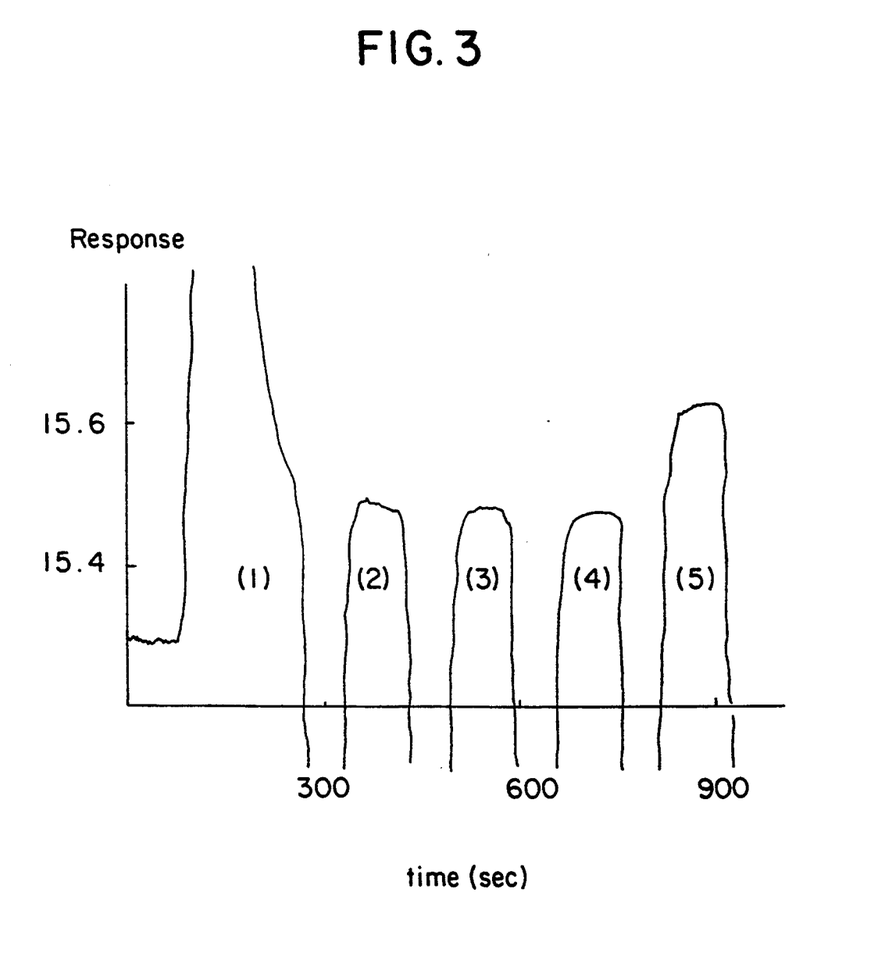
FIG. 3 shows sequential injections of subclass-specific reagents and identification of bound monoclonal as an IgG1 antibody: (1) Monoclonal antibody binds to the surface, this being followed by injections of (2) anti-IgG2a, (3) anti-IgG3, (4) anti-IgG2b, and (5) anti-IgG1 (which binds to the surface).

III.1 Determinations of concentrations and subclass identities of monoclonal antibodies Culture medium with monoclonal antibodies was injected after covalent immobilization of RAMLC antibodies onto the sensing surface (Example II.3). FIG. 1 shows the response curve obtained with (1) injection of culture medium, (2) injection of culture medium containing monoclonal antibody, and (3) regeneration with 0.1 M glycine pH 2.5. FIG. 2 shows the standard curve for various concentrations of a monoclonal IgG1 antibody. Within the range of 5–100 μg antibody per ml the accuracy of the dose-response curve is better than ±10 %. FIG. 3 shows sequential injections of subclass-specific reagents and identification of bound monoclonal as an IgG1 antibody: (1) Monoclonal antibody binds to the surface, this being followed by injections of (2) anti-IgG2a, (3) anti-IgG3, (4) anti-IgG2b, and (5) anti-IgG1 (which binds to the surface). To verify that the system is reversible and repeatable, the antibody binding and subclass identification have been repeated 100 times on the same surface.

III.2 Affinity studies and kinetic studies with anti-theophylline conjugates as carriers of sensor molecules Protein A and protein G were introduced to a theophylline surface in the form of conjugates with an anti-theophylline antibody (chimaeric molecules). In this way we could study the interactions between protein A or protein G and monoclonal antibodies of different subclasses.

Preparation of conjugates

Monoclonal anti-theophylline antibody No. 459, monoclonal antibodies of various different IgG subclasses, monoclonal anti-IgE antibodies of IgG1 subclass No. E164, 95 and 121 and IgE were obtained from Pharmacia Diagnostics AB. The anti-theophylline antibody was digested with pepsin to form F(ab)'-2 fragments or was employed as the intact antibody. Protein A, protein G and SPDP were obtained from Pharmacia LKB Biotechnology AB.

Protein A—anti-theophylline conjugate was prepared by means of SPDP modification of both of these molecules in accordance with the method described by Carlsson et al. (1978). After reduction of modified protein A with 10 mM DTE (1,4-dithioerythritol), 3.8 mg of anti-theophylline having a modification degree of 1.8 (pyridyldisulfide groups per molecule) were mixed with 13.8 mg of reduced protein A having a modification degree of 1.3 (thiols/molecule).

Conjugation was allowed to proceed overnight in 0.1 M phosphate buffer with 0.1 M sodium chloride at pH 7.7. Conjugates of protein G with F(ab)'-2 fragments of anti-theophylline were prepared in an analogous manner.

ANALYSIS

Sensing surfaces with bound theophylline are readily functionalizable with the above-described conjugates. With two parallel sensing surfaces, one of them functionalized with the protein A conjugate and the other with the protein G conjugate, it was possible to very quickly compare the affinities of protein A and protein G, respectively, for a series of immunoglobulins. The results obtained confirmed the differences in these respects as reported by, e.g., Guss et al. (1986).

This experiment demonstrates not only the possibility of rapidly carrying out qualitative measurements of kinetics and affinities but also the flexibility of the techniques employing a sensing surface according to the invention, inasmuch as, with the appropriate reagent in each respective case, such a sensing surface is utilizable for a wide range of different assays.

III.3 Assay for beta-2-microglobulin using the so-called sandwich procedure

Measurement of beta-2-microglobulin (Pharmacia Diagnostics AB) was carried out with a sensing surface containing anti-beta-2-microglobulin antibodies according to Example II.2. The measuring signal for the beta-2-microglobulin binding to the sensing surface was recorded as a function of its concentration in solution, both directly (primary response) and after signal enhancement by means of a secondary immunosorbent-purified antibody which binds to the surface via the primarily bound beta-2-microglobulin to thus form a so-called sandwich structure (secondary response). This obvious and experimentally simple procedure provides an at least 10 times lower detection level.

IV Determination of the amount of adsorbed protein to sensing surfaces

Figure 4:
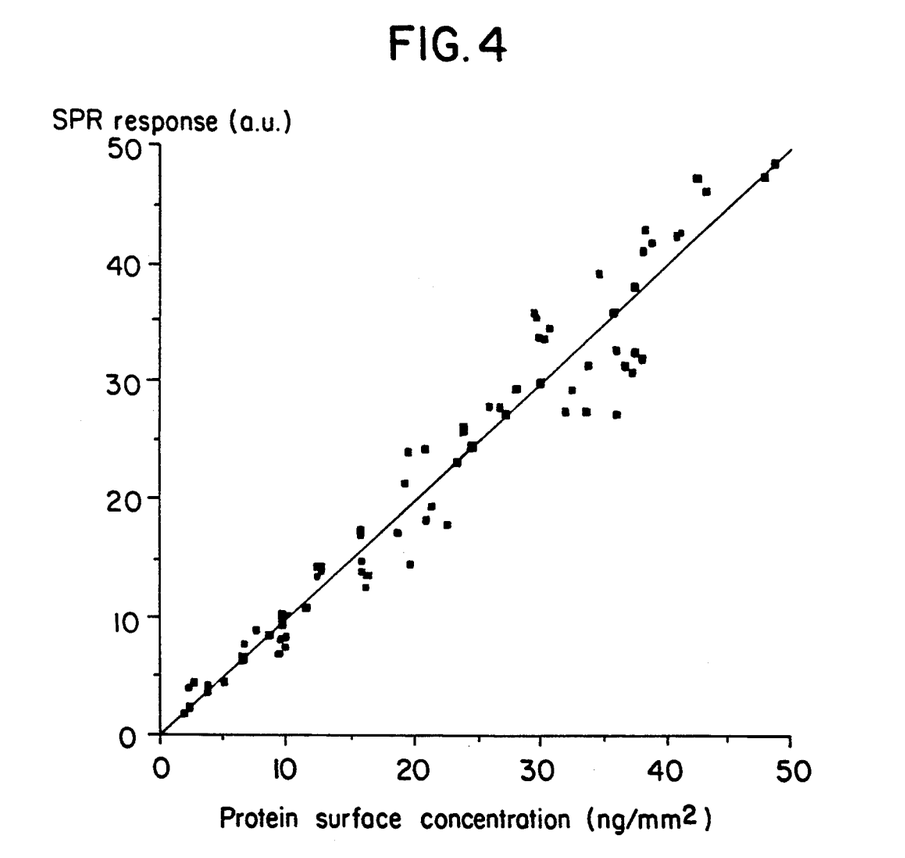

The quantification of the amount of proteins adsorbed to the carboxymethyl modified dextran surface described in I.3.1 was conducted using a radioactive method. Thus, a $^{14}C$- or $^{35}S$-labelled protein (immunoglobulin G, chymotrypsinogen A and transferrin) was concentrated by ion-exchange to a surface placed in an SPR measuring device. The change in angle was measured whereafter the surface was dried and removed from the SPR measuring device. The amount of $^{14}C$-labelled protein on the surface was then quantified in a device which measured the beta-radiation form the surface. Calibration of the radioactive method gave the absolute value of the surface concentration of adsorbed protein. FIG. 4 shows the correlation of the response from the SPR measuring device with the surface concentration obtained from the beta-radiation measurement, for 78 determinations made under various experimental conditions. Surfaces with protein concentrations up to 50 ng/mm$^2$ were obtained, corresponding to approximately 10 dense monolayers of transferrin. This shows the capacity of the described hydrogel and demonstrates the great measuring signal enhancing effect achieved by using a sensing surface with a biocompatible porous matrix according to the present invention. Similar surface concentrations were reached by immobilizing proteins to surfaces with reactive ester functions, which also point out the possibility of making "multilayer-couplings" of proteins for enhanced dynamics in various SPR measurements.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

REFERENCES

Boguslaski RC et al. (1980), Immunoassays: Clinical Laboratory Techniques for the 1980s, Ed. Nakamura RM, Dito WR & Tucker ES III; ARL. New York 1980, pp. 45–64

Brocklehurst K et al (1973), Biochem J 133: 573

Carlson J et al. (1978), Biochem J 173: 723

Crossland RK et al. (1970), J Org Chem 35: 3195

Cullen DC et al. (1978/88), Biosensors 3: 211–225

Ghosh SS et al. (1987), J Org Chem 52: 862

Guss B et al. (1986), The EMBO Journal 5(7): 1567–1575

Liedberg B et al. (1983), Sensors and Actuators 4: 299–304

Merrill et al. (1986), Hydrogels in Medicine and Pharmacy, Vol III, Ed. Peppas NA, chapter 1, CRC Press Nuzzo RG et al. (1983), J Am Chem Soc 105: 4481–4483

O'Shannessy DJ (1985), J Appl Biochem 7: 347

Porter MD et al. (1987), J Am Chem Soc 109: 3559–3568

Raether H (1977), Physics of Thin Films, Ed. Hass G, Francombe M and Hoffman R, Academic Press, New York, pp. 145–261

Regen SL et al. (1986), J Am Chem Soc 108: 6094–6095

Ringsdorf H et al (1988), Angew Chem Int Ed Engl 27: 113-158

Troughton EB et al. (1988), Langmuir 4: 365-385

Volante RP (1981), Tetrahedron Lett 22: 3119

We claim:

1. A sensing surface suitable for use in a biosensor, comprising:
   a film, having two faces, of a free electron metal selected from the group consisting of copper, silver, aluminum and gold; and
   a densely packed monolayer of an organic molecule X-R-Y coated on one of the faces of said film where X is a group selected from the group consisting of
   asymmetrical or symmetrical disulfide (-SSR'Y', -SSRY), sulfide (-SR'Y', -SRY), diselenide (-SeSeR'Y', -SeSeRY), selenide (SeR'Y', -SeRY),
   thiol (-SH), isonitrile, nitro (-NO$_2$), selenol (-SeH), trivalent phosphorous compounds, isothiocyanate, xanthate, thiocarbamate, phosphine,
   thio acid and dithio acid (-COSH, -CSSH)
   where R and R' are hydrocarbon chains, optionally interrupted by hetero atoms, of a length exceeding 10 atoms, wherein in the case of an asymmetrical molecule, R' or R may be H, and Y and Y' are active groups for covalently binding ligands or a biocompatible porous matrix.

2. The sensing surface according to claim 1, which contains a biocompatible porous matrix which is bound to the densely packed monolayer X-R-Y and via which a desired ligand can be bound.

3. The sensing surface according to claim 2, wherein the biocompatible porous matrix is a hydrogel.

4. The sensing surface according to claim 3, wherein the hydrogel is derivatized to contain hydroxyl, carboxyl, amino, aldehyde, carbonyl, epoxy or vinyl groups for immobilizing a desired ligand, and optionally a biospecific ligand bound via said group.

5. The sensing surface according to claim 3, wherein the hydrogel is a polysaccharide selected from the group consisting of agarose, dextran, carrageenan, alginic acid, starch and cellulose and a derivative of any of these.

6. The sensing surface according to claim 3, wherein the hydrogel is a polysaccharide or a swellable organic polymer.

7. The sensing surface according to claim 6, wherein the hydrogel is activated to contain (i) charged groups for bringing about a concentration of biomolecules carrying an opposite charge to that of said charged groups, and (ii) reactive groups for covalently binding the biomolecules concentrated to the sensing surface.

8. The sensing surface according to claim 7, wherein the charged groups are carboxyl groups and the reactive groups are reactive esters, hydrazides or reactive disulfide-containing derivatives.

9. The sensing surface according to claim 8, wherein the reactive disulfide-containing derivative is formed via reaction between reactive ester and 2-(2-pyridinyldithio)ethanamine.

10. The sensing surface according to claim 8, wherein said hydrogel contains a 2-aminoethanethiol derivative.

11. The sensing surface according to claim 6, wherein the hydrogel consists of dextran.

12. The sensing surface according to claim 11, wherein the dextran is derivatized to contain carboxyl, amino, aldehyde, carbonyl, epoxy or vinyl groups for immobilizing the desired ligand, and optionally a biospecific ligand bound via said group or hydroxy groups in the dextran.

13. The sensing surface according to claim 11, wherein the dextran has been activated to contain (i) charged groups for bringing about a concentration of biomolecules carrying an opposite charge to that of said charged groups, and (ii) reactive groups for covalently binding the biomolecules concentrated to the sensing surface.

14. The sensing surface according to claim 13, wherein the dextran has been activated with carboxyl groups part of which have been activated to the form of reactive esters, hydrazides, thiols or reactive disulfide-containing derivatives.

15. The sensing surface according to claim 14, wherein said dextran contains a 2-aminoethanethiol derivative.

16. The sensing surface according to claim 14, wherein the reactive disulfide-containing derivative is formed via reaction between reactive ester and 2-(2-pyridinyldithio)ethanamine.

17. The sensing surface according to claim 1, which contains a ligand which is bound to the densely packed monolayer X-R-Y.

18. The sensing surface according to claim 1, wherein R and R' are hydrocarbon chains, optionally interrupted by heteroatoms containing 12-40 atoms.

19. The sensing surface according to claim 1, wherein Y and Y' are the same.

20. The sensing surface according to claim 1, wherein Y and Y' are hydroxyl, carboxyl, amino, aldehyde, hydrazide, carbonyl, epoxy or vinyl groups.

21. The sensing surface according to claim 1, wherein the hydrogel is a swellable organic polymer selected from the group consisting of polyvinyl alcohol, polyacrylic acid, polyethylene glycol or polyacrylamide.

22. A sensing element suitable for use in a biosensor, comprising:
    a substrate;
    a film of a free electron metal selected from the group consisting of copper, silver, aluminum and gold disposed on said substrate, said film having a first and second major surface, said first major surface being in contact with said substrate; and
    a densely packed monolayer of an organic molecule X-R-Y coated on said second major surface of said film where X is a group selected from the group consisting of
    asymmetrical or symmetrical disulfide (-SSR'Y', -SSRY), sulfide (-SR'Y', -SRY), diselenide (-SeSeR'Y', -SeSeRY), selenide (SeR'Y', -SeRY),
    thiol (-SH), isonitrile, nitro (-NO$_2$), selenol (-SeH), trivalent phosphorus compounds, isothiocyanate, xanthate, thiocarbamate, phosphine,
    thio acid and dithio acid (-COSH, -CSSH),
    where R and R' hydrocarbon chains, optionally interrupted by hetero atoms, of a length exceeding 10 atoms, wherein in the case of an asymmetrical molecule R' or R may be H, and Y and Y' are active groups for covalently binding ligands or a biocompatible porous matrix.

23. The sensing surface according to claim 22, wherein R and R' are hydrocarbon chains, optionally interrupted by heteroatoms, containing 12-30 atoms.

24. The sensing surface according to claim 22, wherein Y and Y' are the same.

25. The sensing surface according to claim 22, where Y and Y' are hydroxyl, carboxyl, amino, aldehyde, hydrazide, carbonyl, epoxy or vinyl groups.

26. A sensing surface suitable for use in a biosensor comprising:
a film, having two faces, of a free electron metal selected from the group consisting of copper, silver, aluminum and gold; and a monolayer of an organic molecule X-R-Y coated on one of the faces of said film where X is a group selected from the group consisting of
asymmetrical or symmetrical disulfide (-SSR'Y', -SSRY), sulfide (-SR'Y', -SRY), diselenide (-SeSeR'Y', -SeSeRY), selenide (SeR'Y', -SeRY), thiol (-SH), isonitrile, nitro (-NO$_2$), selenol (SeH), trivalent phosphorous compounds isothiocyanate, xanthate, thiocarbamate, phosphine, thio acid and dithio acid (-COSH, -CSSH)
where R and R' are hydrogen chains, optionally interrupted by hetero atoms, of a length exceeding 10 atoms, wherein in the case of an asymmetrical molecule, R' or R may be H, Y and Y' are active groups for covalently binding ligands or a biocompatible porous matrix.

27. The sensing surface of claim 26, wherein said monolayer forms an efficient barrier layer which is stable upon storage and which protects said film from chemical corrosion.

* * * * *